United States Patent [19]

Fournier et al.

[11] Patent Number: 4,902,616
[45] Date of Patent: Feb. 20, 1990

[54] PROCESS FOR THE PREPARATION OF CAPSULAR POLYSACCHARIDES OF STAPHYLOCOCCI, THE POLYSACCHARIDES OBTAINED, USES OF THESE POLYSACCHARIDES AND STRAINS FOR CARRYING OUT OF THE PROCESS

[75] Inventors: Jean-Michel Fournier; Anne Bouvet; Alain Boutonnier, all of Paris, France

[73] Assignee: Institut Pasteur, Paris, France

[21] Appl. No.: 227,137

[22] Filed: Aug. 2, 1988

[30] Foreign Application Priority Data

Aug. 3, 1987 [FR] France ................ 87 11006

[51] Int. Cl.⁴ ............... C12P 19/04; C07C 35/08; C07C 35/18
[52] U.S. Cl. .................... 435/101; 435/822; 435/882; 435/883
[58] Field of Search ............. 435/101, 822, 882, 883

[56] References Cited

U.S. PATENT DOCUMENTS 4,460,575  7/1984  d'Hinterland ................ 536/27

FOREIGN PATENT DOCUMENTS 2410043  6/1979  France .

OTHER PUBLICATIONS

Annales Institut Pasteur, vol. 123, 1972, pp. 783–797; J. Fleurette et al.
Chemical Abstracts, vol. 101, No. 11, Sep. 10, 1984, p. 458, No. 88521h, Columbus, OH, U.S.; J. M. Fournier et al.
Chemical Abstracts, vol. 83, No. 7, Aug. 18, 1975, p. 328, No. 56579b, Columbus, OH, U.S.; G. S. Johnsen et al.
Chemical Abstracts, vol. 101, No. 19, Nov. 5, 1984, p. 353, No. 167029g, Columbus, OH, U.S.; Y. Ichiman et al.
Chemical Abstracts, vol. 93, No. 11, Sep. 15, 1980, p. 371, No. 110261p, Columbus, OH, U.S.; A. Umeda et al.
Chemical Abstracts, 93:110261(p), 1980.

Primary Examiner—Ronald W. Griffin
Assistant Examiner—Pamela S. Webber
Attorney, Agent, or Firm—Burns, Doane, Swecker & Mathis

[57] ABSTRACT

The subject of the invention is a process for the preparation of capsular polysaccharides characteristic of *Staphylococcus aureus,* comprising the use of coagulase-negative strains of staphylococci for the preparation of these polysaccharides.

The capsular polysaccharides obtained can be used for the preparation of vaccines against *Staphylococcus aureus* and diagnostic agents.

15 Claims, No Drawings

PROCESS FOR THE PREPARATION OF CAPSULAR POLYSACCHARIDES OF STAPHYLOCOCCI, THE POLYSACCHARIDES OBTAINED, USES OF THESE POLYSACCHARIDES AND STRAINS FOR CARRYING OUT OF THE PROCESS

The present invention relates to a process for the preparation of capsular polysaccharides of the staphylococci and, more particularly, to a process for the preparation of capsular polysaccharides characteristic of *Staphylococcus aureus*

*S. aureus* produces a very large number of extra- and intra-cellular antigens, including numerous toxins and enzymes. It is well established that these metabolites are implicated in food poisoning and in the development of abcesses. On the other hand, it has not been possible to establish any correlation between the presence of these antigens and the invasive properties of *S. aureus*, i.e. its capacity to induce septicemia.

The capsular polysaccharides are well-known factors of pathogenicity in the case of bacteria such as *Streptococcus pneumoniae*, haemophilus influenzae and *Neisseria meninngitidis*. That is the reason why many attempts to isolate capsulated strains of staphylococci have been carried out. Some capsulated strains have been described in the literature (strains Smith, M and T). However, the fact that the strains of *S. aureus* isolated from patients appear to lack capsules when colonies are examined on agar gel or when the microbes are observed under the microscope, has led most workers to conclude that this bacterium is usually not capsulated.

Nevertheless, in publications which have appeared since 1970, Walter W. Karakawa has demonstrated, on the one hand, the existence of capsular polysaccharides in several clinical isolates of staphylococci and, on the other, that capsular antigens protect the bacterium from phagocytosis by the polymorphs. In 1980, Walter Karakawa and Willie Vann (Capsular polysaccharides of *Staphylococcus aureus*. p. 285–293. In J. B Robbins, J. C. Hill, and J. C. Sadoff (ed.). Seminars in infectious disease. vol. 4. Bacterial vaccines. Thieme Stratton. Inc. New York) demonstrated the existence of at least eight capsulated types of *S. aureus* by essentially immunological criteria.

The purification and the biochemical and immunological characterization of the capsular polysaccharide of type 8 were carried out in 1984 (J. M. Fournier et al., Infect. Immun. 45: 87–93) and a method of capsular typing of *S. aureus* was described in 1985 (W. W. Karakawa et al. J. Clin. Microbiol. 22: 445–447).

Epidemiological studies carried out on a large number of strains of *S. aureus* isolated from patients have shown that 70 to 80% of these strains possess one or other of the capsular polysaccharides 5 and 8 (for example, R. D. Arbeit et al. Diagn. Microbiol. Infect. Dis. 2: 85–91. 1984).

Specific monoclonal antibodies to the capsular polysaccharides 5 and 8 have been prepared (H. K. Hochkeppel et al. J. Clin. Microbiol. 25: 526–530. 1987, and M. J. Nelles et al. Infect. Immun. 49: 14–18. 1985).

In addition to *Staphylococcus aureus* which is a coagulase-positive staphylococcus, i.e. one which produces a free coagulase (see Bergey's Manual), many species of staphylococci are known which are coagulase-negative staphylococci, i.e. they do not produce a free coagulase. These coagulase-negative species have been classified by KLOOS and SCHLEIFER (Int. J. Syst. Bacteriol: 25, p. 50–61; p. 62–79).

Of these coagulase-negative species, mention may be made of:
*Staphylococcus simulans*
*Staphylococcus xylosus*
*Staphylococcus cohnii*
*Staphylococcus saprophiticus*
*Staphylococcus haemolyticus*
*Staphylococcus warneri*
*Staphylococcus hominis*
*Staphylococcus epidermidis*
*Staphylococcus capitis*

These coagulase-negative staphylococci are usually not pathogenic for man and animals. A capsular polysaccharide identical with those described for *S. aureus* has not been identified in the strains of the coagulase-negative staphylococci. On the contrary, M. J. Nelles et al (already mentioned) have shown that three strains of *S. epidermidis* do not produce capsular polysaccharides of type 5 or type 8).

Now, the applicant has discovered that certain strains of coagulase-negative staphylocci produce capsular polysaccharides identical with those of *Staphylococcus aureus* and usually in large amounts than *Staphylococcus aureus*. The frequency of isolation of such strains in man is about 2%.

Consequently, the subject of the present invention is a process for the preparation of capsular polysaccharides characteristic of *Staphylococcus aureus*, comprising the use of coagulase-negative strains of staphylococci for the isolation of these capsular polysaccharides.

The subject of the invention is more especially such a process, comprising:

(a) the selection from coagulase-negative strains of staphylococci of a strain producing a capsular polysaccharide characteristic of *Staphylococcus aureus*

(b) culture of the selected strain (c) extraction of the capsular polysaccharide, and (d) purification of the capsular polysaccharide.

Another subject of the present invention is applications of these polysaccharides particularly as vaccines against *Staphylococcus aureus* and diagnostic agents as well as isolated and selected strains producing capsular polysaccharides characteristic of *Staphylococcus aureus*.

The selection of a strain producing a capsular polysaccharide characteristic of *Staphylococcus aureus* can easily be carried out either from the intact bacterium, by agglutination of a bacterial suspension by a means of specific antibodies to the capsular polysaccharides of *Staphylococcus aureus*, in particular monoclonal antibodies such as those already described, used in solution or bound beforehand for example to a support such as latex particles, or by detection of the capsular polysaccharide in bacterial extracts, obtained, for example, by washing the bacteria or after bacterial lysis, brought about by autoclaving or by the use of a specific enzyme for staphylococcus such as lysostaphin.

The presence of the capsular polysaccharide can be demonstrated in these bacterial extracts by immunological methods or by physico-chemical methods.

Of the immunological methods, mention may be made of:

immunoprecipitation in agarose gel (double diffusion), rocket immunoelectrophoresis (in particular, see J. M. Fournier et al. and Hochkeppel et al. already mentioned).

The specific antibody to the capsular polysaccharide is included in an agarose gel equilibrated with a buffer at pH 8.6 (a pH at which antibody does not migrate). The bacterial extract is deposited in a well punched into the gel and then subjected to the action of an electric field which causes a capsular polysaccharide which may be present in the extract to migrate. As it migrates, the capsular polysaccaride combines with the antibody and forms a precipitate, the front of which moves until no free capsular polysaccharide remains. After drying, fixation and staining of the gel, measurement of the height of the spur observed makes it possible to determine the amount of capsular polysaccharide present in the bacterial extract.

immuno-enzymatic reactions of the ELISA type.

Of the physico-chemical methods, mention may be made of the methods which demonstrate the presence of one or more constituents of the capsular polysaccharide:

gas chromatography
high pressure liquid chromatography,
ion exchange chromatography,
gel filtration,
affinity chromatography,
chemical analyses of the aminosugars.

Starting from the selected strains, the capsular polysaccharide is obtained in three steps:

culture of the bacteria,
extraction of the capsular polysaccharide,
purification of the capsular polysaccharide.

(1) Culture of the bacteria:

As culture medium, use may be made in particular of the Columbia medium (Difco), as liquid or solid (enhanced production of capsular polysaccharide by bacteria cultivated on solid medium), the period of culture extending overnight at 37° C., for example.

(2) Extraction of the capsular polysaccharide:

Two processes can be employed:
autoclaving,
lysis of the bacteria by lysostaphin.

(a) Extraction by autoclaving

The bacteria cultivated on a solid medium are suspended in buffered physiological saline (BPS) (5 ml for a Petri dish 9 cm in diameter), and then autoclaved for one hour at 121° C. After centrifugation for 20 minutes at 25000 g, the supernatant is put to one side and the pellet is extracted again under the same conditions. After centrifugation for 20 minutes at 25000 g, the two supernatants are pooled, dialyzed against distilled water and lyophilized. The crude extract (CE) is thus obtained.

Approximately 10 g of moist bacterial pellet and 2 g of CE are obtained from 100 Petri dishes.

The bacteria cultivated in liquid medium are killed by the addition of phenol and ethanol (1.5%, 24 h at laboratory temperature), and are then recovered by centrifugation for 20 minutes at 25000 g or by ultrafiltration for example on a 0.45 micrometer Durapore filter of the HV type obtained from Millipore. The bacterial pellet is resuspended in BPS (0.1 g of moist pellet/ml of BPS) and then extracted by autoclaving under the conditions previously described.

(b) Extraction by means of lysostaphin:

The bacterial pellet is suspended in BPS (0.5 g/ml) containing 25 mg of lysostaphin per liter. The suspension is stirred overnight at 37° C., then centrifuged for 20 minutes at 25000 g. The supernatant is dialyzed against distilled water, and then lyophilized.

(3) Purification of the capsular polysaccharide:

The following is an advantageous method of purification:

(a) Enzymatic treatment of the CE:

The CE is taken up in BPS (10 mg/ml), and treated with DNase and RNase (0.1 mg/ml, 6 h at 37° C.) then with protease (1 mg/ml, overnight at 37° C.). The product is then dialized against distilled water and lyophilized. 2 g of CE gave approximately 0.7 g of enzyme treated extract (ETE). This treatment enables most of the proteins and nucleic acids to be removed.

(b) Ion exchange chromatography:

The ETE is taken up in sodium acetate buffer (0.05M, pH 6) containing sodium chloride (0.1M) and then applied to an ion exchanger (for example DEAE-cellulose) equilibrated with the same buffer. Most of the proteins contained in the ETE are not absorbed on the ion exchanger and are removed by washing the ion exchanger with the equilibration buffer. On the other hand, the capsular polysaccharide, teichoic acid and the nucleic acids remain bound to the ion exchanger.

The capsular polysaccharide is eluted by applying to the ion exchanger a buffer containing a higher concentration of sodium chloride. As an example, the capsular polysaccharide of type 5 is eluted with a sodium acetate buffer (0.05M, pH 6) containing sodium chloride at a concentration of 0.15M. In order to elute the capsular polysaccharide of type 8, the concentration of sodium chloride must be 0.18M. The eluates are recovered in a fraction collector and the fractions which contain the capsular polysaccharide (detected by an immunological reaction using specific antibodies) are pooled, dialyzed against distilled water and then lyophilized.

Approximately 20 mg of extract purified by ion exchange (IEE) are obtained starting from 0.7 g of ETE. This ion exchange chromatography enables the large majority of proteins, nucleic acids and teichoic acid to be removed.

(c) Gel filtration:

The IEE is redissolved in a sodium chloride solution (0.2M) and filtered through a Sepharose 4B-CL gel. The fractions containing the capsular polysaccharide, detected by an immunological reaction, are pooled, dialyzed against distilled water and lyophilized. The lyophilized product constitutes the purified capsular polysaccharide.

The capsular polysaccharide is contaminated by less than 1% of proteins, less than 0.5% of nucleic acids and less than 0.05% of teichoic acid. Starting from 20 mg of IEE, approximately 10 mg of purified capsular polysaccharide are obtained. Over-all, starting from 10 g of moist bacterial pellet harvested from 100 Petri dishes, approximately 10 mg of purified capsular polysaccharide are obtained.

As examples, the following strains of coagulase-negative staphylococci producing the capsular polysaccharide identical with that of *Staphylococcus aureus* have been isolated.

In order to select strains producing capsular polysaccharides characteristic of *Staphylococcus aureus*, the bacterial suspension is placed in contact with antibodies specific for these capsular polysaccharides. The detection of the capsular polysaccharides obtained after bacterial lysis was performed by rocket immunoelectrophoresis (method described by J. Mo. FOURNIER already mentioned) or by Elisa.

Each strain producing large amounts of capsular polysaccharides was characterized by these two methods.

| Number of the strain | 850206 | 860638 | 850071 | 850279 |
|---|---|---|---|---|
| File number with the CNCM | I—685 | I—682 | I—684 | I—683 |
| Morphology | Cocci gram | Cocci gram | Cocci gram | Cocci gram |
| Catalase | + | + | + | + |
| Fermentation of glucose in MEVAG medium | + | + | + | + |
| DNAse | − | − | − | − |
| Coagulase | − | − | − | − |
| Capsular type | 5 | 5 | 8 | 8 |

| Number of the strain | 850206 | 860638 | 850071 | 850279 |
|---|---|---|---|---|
| D-Glucose | + | + | + | + |
| D-Fructose | + | + | + | + |
| D-Mannose | ± | + | + | + |
| Maltose | + | + | + | + |
| Lactose | − | + | + | + |
| D-Trehalose | + | + | + | + |
| D-Mannitol | − | − | − | − |
| Xylitol | − | − | − | − |
| D-Melibiose | − | − | − | − |
| Potassium nitrate | + | − | + | + |
| α-naphthyl phosphate | − | − | − | − |
| Sodium pyruvate | + | − | + | − |
| Raffinose | − | − | − | − |
| Xylose | − | − | − | − |
| Sucrose | + | + | + | + |
| α-methyl-D-glucoside | − | − | − | − |
| N—acetyl-glucosamine | + | + | + | + |
| Arginine | + | − | − | − |
| Urea | − | + | − | − |
| Species* | Staphylococcus haemolyticus 1 | Staphylococcus hominis 2 | Staphylococcus hominis 2 | Staphylococcus hominis 2 |

*according to the classification of Kloos and Schleifer

These strains exhibit the following antibiotic spectra:

| Number of the strain | 850206 | 860638 | 850071 | 850279 |
|---|---|---|---|---|
| Penicillin G | R | S | S | R |
| Oxacillin | R | S | S | S |
| Tobramycin | R | S | S | S |
| Gentamicin | R | S | S | S |
| Tetracycline | R | S | S | R |
| Erythromycin | R | R | S | S |
| Clindamycin | S | S | S | S |
| Pristinamycin | S | S | S | S |
| Trimethoprim + Sulfamides | R | S | S | S |
| Rifampicin | S | S | S | S |
| Fusidic acid | R | S | S | S |
| Vancomycin | S | S | S | S |

R = resistant
S = sensitive

As an example, the implementation of the procedure for preparing the capsular polysaccharides extracted by autoclaving of $10^9$ bacteria makes it possible to obtain the amounts indicated in the table below. These values are given only as an indication since the production of capsular polysaccharide is quite variable from one culture to another.

| Number of the strain | Species | Capsular type | Production of capsular polysaccharide (microgrammes) |
|---|---|---|---|
| 850206 | S. haemolyticus 1 | 5 | 30 |
| 860638 | S. hominis 2 | 5 | 4 |
| 850071 | S. hominis 2 | 8 | 20 |
| 850279 | S. hominis 2 | 8 | 5 |

The capsular polysaccharides obtained from strains of coagulase-negative staphylococci can be used for:

(a) the preparation of vaccines against *Staphylococcus aureus* for human or veterinary use, with a view to protection of the individual or the production of immune sera which can be used for the preparation of anti-capsular polysaccharide antibodies which can be used in passive immunotherapy or for diagnosis using agglutination techniques, ELISA, RIA or Western blot according to methods known to the person skilled in the art;

(b) the preparation of diagnostic agents for diagnosis in man, in animals or in agri-foodstuffs, and in particular for:

the detection in biological products of specific antibodies to the capsular polysaccharide, and the detection of capsular polysaccharides in chemical isolates of coagulase-positive or coagulase-negative staphylococci.

We claim:

1. A process for the preparation of capsular polysaccharides characteristic of *Staphylococcus aureus*, comprising using strains of coagulase-negative staphylococci which have the ability to produce capsular polysaccharides.

2. A process for the preparation of capsular polysaccharides characteristic of *Staphylococcus aureus*, said process comprising:
   (a) selecting from coagulase-negative strains of staphylococci a strain which is capable of producing a capsular polysaccharide characteristic of *Stapylococcus aureus*,
   (b) culturing the selected strain from (a),
   (c) extracting the capsular polysaccharide from said cultured selected strains, and
   (d) purifying the capsular polysaccharide.

3. Process according to claim 2, wherein the selection of a coagulase-negative strain of staphylococci producing a capsular polysaccharide characteristic of *Staphylococcus aureus* is carried out by an agglutination reaction using antibodies specific for the capsular polysaccharides of *Staphylococcus aureus*.

4. Process according to claim 2, wherein the selection of a coagulase-negative strain of staphylococci producing a capsular polysaccharide characteristic of *Staphylococcus aureus* is carried out by detection of the capsular polysaccharide in a bacterial extract of the strain.

5. Process according to claim 4, wherein said bacterial extract is obtained by washing the bacteria.

6. Process according to claim 4, wherein said bacterial extract is obtained after bacterial lysis.

7. Process according to claim 2, wherein the capsular polysaccharide is extracted after autoclaving.

8. Process according to claim 2, wherein the capsular polysaccharide is extracted after lysis of the bacteria by a lytic agent.

9. Process according to claim 2, wherein the extracted capsular polysaccharide is purified by enzymatic treatment, followed by ion exchange chromatography and gel filtration.

10. Process according to claim 1, comprising the use of a coagulase-negative strain of staphylococci deposited with the CNCM under the numbers I-682, I-683, I-684 or I-685.

11. Capsular polysaccharide characteristic of *Staphylococcus aureus* and obtained from strains of coagulase-negative staphylococci.

12. Vaccine against *Staphylococcus aureus* comprising a capsular polysaccharide characteristic of *Staphylococcus aureus* and obtained from strains of coagulase-negative staphylococci.

13. Purified strains of coagulase-negative staphylococci producing capsular polysaccharides characteristic of *Staphylococcus aureus*.

14. Strains according to claim 13, which are the strains deposited with the CNCM under the numbers I-682, I-683, I-684 and I-685.

15. A diagnostic agent for the detection of coagulase-positive or coagulase-negative staphylococci comprising a capsular polysaccharide characteristic of *Staphylococcus aureus* which is obtained from strains of coagulase-negative staphylococci.

* * * * *